United States Patent [19]

Kiener et al.

[11] Patent Number: 5,182,197
[45] Date of Patent: Jan. 26, 1993

[54] MICROBIOLOGICAL PROCESS FOR THE PRODUCTION OF 6-HYDROXYPICOLINIC ACID

[75] Inventors: Andreas Kiener, Visp; Rainer Glockler; Klaus Heinzmann, both of Visperterminen, all of Switzerland

[73] Assignee: Lonza Ltd., Basel, Switzerland

[21] Appl. No.: 830,844

[22] Filed: Feb. 4, 1992

[30] Foreign Application Priority Data

Feb. 4, 1991 [CH] Switzerland .......................... 330/91

[51] Int. Cl.$^5$ .................. C12P 17/12; C12R 1/01; C12R 1/05
[52] U.S. Cl. ................................. 435/122; 435/252.1; 435/252.5; 435/252.6; 435/822; 435/829; 435/874
[58] Field of Search ................. 435/122, 829, 252.1, 435/252.6, 252.5, 822, 874, 814

[56] References Cited

U.S. PATENT DOCUMENTS

| | | | |
|---|---|---|---|
| 4,859,592 | 8/1989 | Hagedorn et al. | 435/122 |
| 5,082,777 | 1/1992 | Lehky et al. | 435/122 |
| 5,104,798 | 4/1992 | Kiener | 435/122 |

OTHER PUBLICATIONS

R. L. Tate et al., *Canadian Journal of Microbiology*, vol. 20, No. 5, (May 1974), pp. 695 to 702.

O. P. Shukla et al., *Indian Journal of Biochemistry and Biophysics*, vol. 10, No. 1, (Mar. 1973), pp. 176 to 178.
*Tetrahedron Letters*, vol. 29, (1988), pp. 4389 to 4392.
Shukla, O. and S. M. Kaul, Indian J. of Biochemistry and Biophysics, vol. 10, (1973), pp. 176 to 178.
Shukla O., et al., Indian J. of Biochemistry and Biophysics, vol. 14, (1977), pp. 292 to 295.
Tate, R. L. and J. C. Ensign, Can. J. Microbiol., vol. 20, (1974), pp. 695 to 702.
*Berichte der Deutschen Chemischen Gesellschaft*, (Reports of the German Chemical Society), 45, (1912), pp. 2456 to 2467.
Drews, Gerhart, Mikrobiologisches Praktikum (Microbiological Workshop), 4th Ed., Springer Verlag, (1983), pp. 1 to 85.

*Primary Examiner*—Herbert J. Lilling
*Attorney, Agent, or Firm*—Fisher, Christen & Sabol

[57] ABSTRACT

A microbiological process for the production of 6-hydroxypicolinic acid starting from picolinic acid and/or its salts. The concentration of picolinic acid and/or its salts is selected so that the 6-hydroxypicolinic acid is not further metabolized. The process is performed either by microorganisms of genus Pseudomonas, Bacillus, Alcaligenes, Aerococcus, or Rhodotorula, or with biomass using picolinic acid, which grow with picolinic acid as the sole carbon, nitrogen and energy source.

4 Claims, No Drawings

MICROBIOLOGICAL PROCESS FOR THE PRODUCTION OF 6-HYDROXYPICOLINIC ACID

BACKGROUND OF THE INVENTION

1. Field Of the Invention

The invention relates to a microbiological process for the production of 6-hydroxypicolinic acid, starting from picolinic acid and/or its salts.

2. Background Art

Several methods for the production of 6-hydroxypicolinic acid by organic syntheses are known. From picolinic acid, for example, the 6-hydroxypicolinic acid can be obtained by reaction with potassium hydroxide [Tetrahedron Letters, Vol. 29, (1988), pages 4389 to 4392]. A drawback of such process is that the 6-hydroxypicolinic acid is obtained only in moderate yield (51 percent).

It is also known that microorganisms of genus Bacillus hydroxylate picolinic acid to 6-hydroxypicolinic acid [O. Shukla and S. M. Kaul, Indian J. of Biochemistry and Biophysics, Vol. 10, (1973), pages 176 to 178; O. Shukla et al., Indian J. of Biochemistry and Biophysics, Vol. 14, (1977), pages 292 to 295]. A great drawback of such process is that the further metabolization of the 6-hydroxypicolinic acid can be stopped only with the inhibitor sodium arsenite, and thus the growth of the microorganisms also is inhibited. Another drawback consists in that 6-hydroxypicolinic acid is not exclusively formed, but instead a mixture of 3,6-dihydroxypicolinic acid and 6-hydroxypicolinic acid is formed.

R. L. Tate and J. C. Ensign, Can. J. Microbiol., Vol. 20, (1974), pages 695 to 702, describes the hydroxylation of picolinic acid with microorganisms of genus Arthrobacter. Drawbacks of such process are that these microorganisms cannot exclusively use picolinic acid as a carbon, nitrogen and energy source, but in the hydroxylation, a yeast extract has to be present, which can lead to undesirable impurities of the product. Another drawback lies in the fact that the 6-hydroxypicolinic acid is formed only in the case of low oxygen content, and the microorganisms are not present in the growth phase, and thus little product is formed.

BROAD DESCRIPTION OF THE INVENTION

The main object of the invention is to eliminate the above-described drawbacks and to provide an economical, microbiological process for the production of 6-hydroxypicolinic acid, in which the product is formed in high purity and with high yield. Other objects and advantages of the invention are set out herein or obvious herefrom to one skilled in the art.

The objects and advantages of the invention are achieved by the processes and microorganisms of the invention.

The invention includes a variant of a microbiological process for the production of 6-hydroxypicolinic acid. In such process variant, picolinic acid and/or its salts are hydroxylated by a microorganism of the genus Pseudomonas, Bacillus, Alcaligenes, Aerococcus or Rhodotorula, which grows with picolinic acid as the sole carbon, nitrogen and energy source, and the concentration of the picolinic acid and/or it salts is selected so that the 6-hydroxypicolinic acid is not further metabolized.

Preferably the hydroxylation is performed with alcaligenes faecalis, deposited in the DSM under number 6269 or its descendants and mutants. Preferably the concentration of the picolinic acid and/or its salts is selected so that it does not exceed 10 percent by weight. Preferably the hydroxylation is performed at a temperature of 10° to 60° C. and a pH of 4 to 10.

The invention also includes the microorganism Alcaligenes faecalis deposited in the DSM with number 6269 and its descendants and mutants.

The invention further includes another variant of the microbiological process for the production of 6-hydroxypicolinic acid. In such proccess an aerobic biomass using picolinic acid and/or its soluble salts is cultivated with picolinic acid and/or its soluble salts and a mineral acid in a molar ratio of the picolinic acid and/or its soluble salts to the mineral acid of 1 to 8. Such molar ratio is assured over the total cultivation phase. Then the hydroxylation of the picolinic acid and/or its soluble salts is performed with this biomass.

Preferably the molar ratio of picolinic acid and/or its soluble salts to the mineral acid is adjusted by the measurement of the ratio of oxygen to carbon dioxide in the waste gas and/or by the measurement of the pH. Preferably, in the cultivation step, sulfuric acid is used as the mineral acid in a molar ratio of the picolinic acid and/or its soluble salts to the sulfuric acid of 3 to 5. Preferably the cultivation and the hydroxylation are performed at a temperature of 15° to 50° C. and a pH of 5 to 9.

6-Hydroxypicolic acid is used, for example, for the production of 2-oxypyrimidine [Berichte der Deutschen Chemischen Gesellschaft (Reports of the German Chemical Society), 45, (1912), pages 2456 to 2467], which in turn is an important intermediate product for the production of pharmaceutical agents.

DETAILED DESCRIPTION OF THE INVENTION

Herein, the phrase "picolinic acid" is also understood to include its salts, such as, its water-soluble alkali salts, its ammonium salts, etc., and to include, for example, a mixture of picolinic acid and its water-soluble alkali salts.

According to the invention, one variant of the process for the production of 6-hydroxypicolinic acid is performed so that picolinic acid is hydroxylated by a microorganism of the genus Pseudomonas, Bacillus, Alcaligenes, Aerococcus, or Rhodotorula, which grows with picolinic acid as the sole carbon, nitrogen and energy source, and the concentration of the picolinic acid is selected so that the 6-hydroxypicolinic acid is not further metabolized.

As the microorganisms, all of the above-mentioned genuses can be used which grow with picolinic acid as the sole carbon, nitrogen and energy source. The microorganisms, for example, from sewage treatment plants or earth, can be isolated according to methods usual to one skilled in the art.

Preferably, the microorganism Alcaligenes faecalis, which was deposited with number 6269 on Dec. 7, 1990, in the Deutsche Sammlung von Mikroorganismen und Zellkulturen GmbH [German Collection of Microorganisms and Cell Cultures GmbH], Mascherodeweg 1b, D-3300 Brunswick, is used for the production of 6-hydroxypicolinic acid. This microorganism was not previously known.

Properties of the strain Alcaligenes faecalis DSM No. 6269:

| | | | |
|---|---|---|---|
| cell shape | rods | VP | − |
| width micron | 0.5 to 0.8 | | |
| length micron | 1.0 to 2.0 | ODC | − |
| mobility | + | NO₂ from NO₃ | − |
| flagella | peritrichal | denitrification | − |
| gram reaction | − | phenylalanine-desaminase | − |
| lysis by 3% KOH | + | | |
| aminopeptidase (Cerny) | + | levan from saccharose | − |
| spores | − | lecithinase | − |
| oxidase | + | urease | − |
| catalase | + | hydrolysis of starch | − |
| growth | | gelatin | − |
| anaerobic | − | casein | − |
| 37/40° C. | ± | DNA | − |
| pH 5.6 | + | Tween 80 | − |
| MacConkey broth | + | aesculin | − |
| pigments | − | tyrosine catabolism | − |
| nondiffusing | − | | |
| diffusing | − | growth substance requirement | − |
| fluorescent | − | | |
| pyocyanine | − | use of substrate acetate | + |
| acid from (OF test) | | adipate | − |
| aerobic glucose | − | caprate | + |
| anaerobic glucose | − | citrate | + |
| aerobic xylose | − | glycolate | + |
| | | L-lactate | + |
| gas from glucose | − | laevulinate | − |
| | | malate | + |
| acid from (ASS) | | malonate | + |
| glucose | − | phenyl acetate | + |
| fructose | − | propionate | + |
| xylose | − | suberate | − |
| | | L-arabinose | − |
| ONPG | − | fructose | − |
| | | glucose | − |
| ADH | − | mannose | − |
| | | maltose | − |
| LDC | − | xylose | − |
| | | ribose | − |
| VP | − | mannitol | − |
| | | gluconate | − |
| indole | − | 2-ketogluconate | − |
| | | N-acetyl-glucosamine | − |
| | | L-histidine | − |
| | | L-methionine | + |
| | | hydroxybutyrate | + |

For the performance of the picolinic acid hydroxylation, it is desirable that the 6-hydroxypicolinic acid is not further metabolized.

The following parameters have to be met to achieve economic efficiency of the picolinic acid hydroxylation:

(a) The cells should already produce 6-hydroxypicolinic acid during the growth phase.

(b) The picolinic acid hydroxylase is to remain active after the growth has been completed.

(c) The breakdown pathway of the picolinic acid should be inhibited at the stage of the 6-hydroxypicolinic acid.

(d) The product (6-hydroxypicolinic acid) is to be enriched in the growth medium.

Surprisingly, it has now been found that these parameters are met at the same time if the picolinic acid is supplied during the growth of the microorganisms or else after the growth phase of the microorganisms in such a concentration that the 6-hydroxypicolinic acid is not further metabolized.

As mentioned, the strain *Alcaligenes faecalis* DSM No. 6269 grows with picolinic acid as the sole carbon, nitrogen and energy source. The cultivation of the strain *Alcaligenes faecalis* DSM No. 6269 can take place with 0.05 to 0.2 percent by weight of the picolinic acid — the introduced picolinic acid is completely metabolized.

If the picolinic acid concentration is increased, the cellular growth is inhibited and no more growth can be observed over a 0.5 percent by weight of picolinic acid concentration. But the activity of the picolinic acid hydroxylase remains unchanged in the cells.

Suitably, after the cultivation of the microorganisms, the picolinic acid is to be added as 10 percent by weight to saturated solution at such a rate that the concentration of the picolinic acid does not exceed 10 percent by weight in the fermenter. Preferably, the concentration of the picolinic acid in the fermenter does not exceed 1 percent by weight.

Suitably, the picolinic acid solution is used together with an alkali hydroxide solution for pH adjustment of the culture medium. As the alkali hydroxide, for example, sodium hydroxide or potassium hydroxide can be used.

As a culture medium, those usual among experts can be used, preferably a mineral salt medium is used, the composition of which is indicated in Table 2 below.

Suitably, the oxygen content in the culture medium during the hydroxylation is up to 90 percent of the maximum saturation, preferably, the oxygen content lies in a range of 0.1 to 50 percent of the maximum saturation. The hydroxylation of the picolinic acid can take place during or after the growth phase. During or after the growth phase, the pH is suitably between pH 4 and 10, preferably between 5 and 9. The hydroxylation takes place suitably at a temperature of 10° to 60° C., preferably 15° to 40° C.

In addition, to increase the product concentration, an alkali salt of the picolinic acid is fed, in a preferred embodiment of the invention, after the growth phase of the microorganisms, and the feed of the picolinic acid alkali salt is controlled in the fermenter by partial pressure adjustment of oxygen. The alkali salt of the picolinic acid suitably is added at such a rate that the concentration of the picolinic acid salt in the fermenter does not exceed 10 percent by weight, preferably so that it does not exceed 1 percent by weight.

The second variant of the invention process according to the invention for the production of 6-hydroxypicolinic acid takes place so that:

(a) an aerobic biomass using picolinic acid is cultivated with picolinic acid and a mineral acid in a molar ratio of the picolinic acid to the mineral acid of 1 to 8, and such ratio is assured over the entire cultivation phase; and (b) the hydroxylation of the picolinic acid is performed with such biomass.

By the phrase "cultivate an aerobic biomass using picolinic acid", or similar phrase, the following is meant: If a biomass is cultivated, for example, from sewage sludge as an inoculum with the described molar picolinic acid-mineral acid ratio under aerobic conditions, an aerobic biomass using picolinic acid, i.e., an unsterile biomass, is obtained which grows with picolinic acid as the sole carbon, nitrogen and energy source in the presence of oxygen.

The molar ratio of the picolinic acid to the mineral acid, i.e., the feed of the mixture consisting of the picolinic acid and the mineral acid to the cell suspension, is suitably adjusted either by the measurement of the pH and/or by the measurement of the ratio of oxygen to carbon dioxide in the outlet air. As the mineral acids, for example, sulfuric acid, hydrochloric acid, nitric acid or phosphoric acid can be used, preferably sulfuric acid is used. Suitably, the adjustment of the feed of the mixture takes place during the cultivation of the biomass (step a) so that a molar ratio of picolinic acid to sulfuric acid of 3 to 5 is assured (that is, per mole of sulfuric acid, suitably 3 to 5 mol of the picolinic acid is used for the cultivation). Preferably, 4 to 5 mol of picolinic acid per mole of sulfuric acid is used for the cultivation. Usually, the cultivation of the aerobic biomass using picolinic acid takes place in a mineral salt medium, preferably in the mineral salt medium whose composition is described in Table 2 below. The cultivation of the biomass takes place suitably at a pH of 5 to 9, preferably from 6 to 8. Suitably, during the cultivation of the biomass, the temperature is between 15° and 50° C., preferably between 25° and 40° C. Usually, the cultivation of the biomass takes place in a period of 0.5 to 3 days.

After the cultivation, the biomass can then be separated for the actual biotransformation (hydroxylation) either in a way usual to one skilled in the art or the picolinic acid to be hydroxylated is added directly to the cultivated biomass. The actual hydroxylation of the picolinic acid (substrate) then takes place under the same conditions as already described in the first variant.

Suitably, during the hydroxylation, the optical density at 650 nm ($OD_{650}$) of the biomass is between 0.5 and 100, preferably between 1 and 50. The suitable temperature in this variant is between 15° and 50° C., preferably between 25° and 40° C., and the pH is suitably between 5 and 9, preferably between 6 and 8.

After the separation of the cells from the culture medium, e.g., by centrifuging or microfiltration, the clear solution can be acidified, and the 6-hydroxypicolinic acid precipitates. To make possible an optimum formation of crystals, the solution is preferably acidified at 60° C. But the clear solution can also be used also without working up for further reactions.

EXAMPLE 1

Isolation of *Alcaligenes faecalis* (DSM 6269)

Aerobic picolinic acid-metabolizing microorganisms were enriched in the A+N medium (see Table 1 below) by adding 0.1 percent (w/v) picolinic acid as the sole carbon and energy source. The general techniques for isolating microorganisms are described, for example, in G. Drews. Mikrobiologisches Praktikum [Microbiological Workshop], 4th edition, Springer Verlag, (1983), pages 1 to 85. Samples from the earth or sewage treatment plants were used as an inoculum. The concentrations were cultivated in shaking flasks at 30° C. After inoculating three times in fresh medium, the concentrations were plated out in the same medium by adding 16 g of agar per liter and incubated at 30° C. After repeated plating out on the agar medium, pure cultures were able to be isolated.

EXAMPLE 2

Hydroxylation in the growth phase

*Alcaligenes faecalis* (DSM 6269) was aerobically cultivated in a mineral salt medium (see Table 2 below) with picolinic acid as the sole carbon, nitrogen and energy source at pH 7 and at a temperature of 30° C. For cultivation, a 20 liter fermenter with a working volume of about 15 liters was used. For pH adjustment, a 4.06 mol/l (50 percent w/v, about 2 liters) picolinic acid solution and a 3 mol/l (12 percent w/v, <20 ml) of sodium hydroxide solution were added within 27 hours. Then, 0.14 mol/l (2 percent w/v) of 6-hydroxypicolinic acid and 16 mmol/l (0.18 percent w/v) of picolinic acid were detected in the fermentation solution. At that time, the oxygen content at an air throughput of 30 l/min and at a stirring speed of 750 rpm was 1 percent saturation.

Hydroxylation after the growth phase

After the growth phase, a 2.7 mol/l (47 percent w/v, about 2.5 liter) sodium picolinate solution (pH 7) was added within 15 hours in the fermenter. The metering speed of the sodium picolinate solution was controlled by the oxygen partial pressure adjustment of the fermenter so that the oxygen content did not exceed a saturation of 20 percent, and the concentration of the picolinate was about 20 mmol/l (0.22 percent w/v). At a concentration of 0.7 mol/l (9.8 percent w/v) of 6-hydroxypicolinic acid and a fermentation time of a total of 42 hours, the batch was terminated. For the batch, a total of 17.8 mol (2190 g) of picolinic acid was used in the form of the free acid and as the sodium salt. 13.3 mol (1850 g) of 6-hydroxypicolinic acid was able to be isolated from picolinic acid or its sodium salt in crystalline form after the acidification of the cell-free solution, which corresponded to a yield of 74 percent, relative to the picolinic acid used. According to HPLC analysis, the purity of the 6-hydroxypicolinic acid was more than 95 percent. In the clear filtrate, 0.13 mol (18.5 g) of 6-hydroxypicolinic acid, corresponding to 0.75 percent of the picolinic acid used and 0.3 mol (37 g) of picolinic acid, corresponding to 1.7 percent of the picolinic acid used, were detectable.

EXAMPLE 3

Production of 6-hydroxypicolinic acid (with unsterile biomass)

(a) Cultivation

The fermentation was performed in an unsterile mineral salt medium (see Table 2 below), in a fermenter with a working volume of 5 liters at pH 7.0, at a temperature of 30° C. and an aeration rate between 0.5 to 5.0 liters per minute. For pH adjustment, a mixture of 307 g of picolinic acid (2.5 mol) and 49 g (0.5 mol) of $H_2SO_4$ and 1 liter of water were added to a medium. The fermenter was inoculated with 200 ml of sewage sludge from the waste water purification plant, Zermatt, Switzerland. After 48 hours, the fermenter was emptied to a half liter and filled with fresh, unsterile medium. After another 24 hours, the process was repeated.

(b) Hydroxylation in the growth phase

As the last batch described under (a) had reached an $OD_{650}$ nm of 1, the hydroxylation was begun. The pH adjustment took place from that time on by the corresponding addition of a 50 percent (w/v) picolinic acid solution. In addition, a 59 percent (w/v) sodium picolinate solution was added with an average metering rate of 7.3 ml·h$^{-1}$ was added to the fermenter over a period of 68 hours. At the end of the hydroxylation phase, no picolinic acid was able to be detected spectrophotometrically. The end concentration of 6-hydroxypicolinic acid (analytical) was 51 g/l.

TABLE 1

| A + N medium | |
|---|---|
| Composition | Concentration (mg/l) |
| $(NH_4)_2SO_4$ | 2000 |
| $Na_2HPO_4$ | 2000 |
| $KH_2PO_4$ | 1000 |
| NaCl | 3000 |
| $MgCl_2.6H_2O$ | 400 |
| $CaCl_2.2H_2O$ | 14 · 5 |
| $FeCl_3.6H_2O$ | 0 · 8 |
| pyridoxal-hydrochloride | $10 \cdot 10^{-3}$ |
| riboflavin | $5 \cdot 10^{-3}$ |
| nicotinic acid amide | $5 \cdot 10^{-3}$ |
| thiamin hydrochloride | $2 \cdot 10^{-3}$ |
| biotin | $2 \cdot 10^{-3}$ |
| pantothenic acid | $5 \cdot 10^{-3}$ |
| p-aminobenzoate | $5 \cdot 10^{-3}$ |
| folic acid | $2 \cdot 10^{-3}$ |
| vitamin B12 | $5 \cdot 10^{-3}$ |
| $ZnSO_4.7H_2O$ | $100 \cdot 10^{-3}$ |
| $MnCl_2.4H_2O$ | $90 \cdot 10^{-3}$ |
| $H_3BO_3$ | $300 \cdot 10^{-3}$ |
| $CoCl_2.6H_2O$ | $200 \cdot 10^{-3}$ |
| $CuCl_2.2H_2O$ | $10 \cdot 10^{-3}$ |
| $NiCl_2.6H_2O$ | $20 \cdot 10^{-3}$ |
| $Na_2MoO_4.2H_2O$ | $30 \cdot 10^{-3}$ |
| $EDTANa_2.2H_2O$ | $5 \cdot 10^{-3}$ |
| $FeSO_4.7H_2O$ | $2 \cdot 10^{-3}$ |

(The pH of the solution was adjusted to 7.0 after adding picolinic acid.)

TABLE 2

| Mineral salt medium composition: | |
|---|---|
| picolinic acid | 2 g/l |
| $MgCl_2.6H_2O$ | 0.8 g/l |
| $CaCl_2$ | 0.16 g/l |
| $Na_2SO_4$ | 0.25 g/l |
| $KH_2SO_4$ | 0.4 g/l |
| $Na_2HPO_4$ | 0.9 g/l |
| trace elements | 1 ml/l |
| Composition of the trace element solution: | |
| picolinic acid | 200 g/l |
| NaOH | 65 g/l |
| $ZnSO_4.7H_2O$ | 9 g/l |
| $MnCl_2.4H_2O$ | 4 g/l |
| $H_3BO_3$ | 2.7 g/l |
| $CoCl_2.6H_2O$ | 1.8 g/l |
| $CuCl_2.2H_2O$ | 1.5 g/l |
| $NiCl_2.6H_2O$ | 0.18 g/l |
| $Na_2MoO_4.2H_2O$ | 0.2 g/l |
| $FeSO_4.7H_2O$ | 30 g/l |

(The pH of the solution was adjusted to 7.0.)

What is claimed is:

1. A microbiological process for the production of 6-hydroxypicolinic acid, characterized in that picolinic acid and/or at least one of its salts are hydroxylated by microorganism *Alcaligenes faecalis*, deposited in the DSM under number 6269, or one of its descendants or mutants, which grows with picolinic acid as sole carbon, nitrogen and energy source, and that the concentration of the picolinic acid and/or at least one of its salts is selected so that the 6-hydroxypicolinic acid is not further metabolized.

2. The process according to claim 1 wherein the concentration of the picolinic acid and/or at least one of its salts is selected so that it does not exceed 10 percent by weight.

3. The process according to claim 2 wherein the hydroxylation is performed at a temperature of 10° to 60° C. and at a pH of 4 to 10.

4. The process according to claim 1 wherein the hydroxylation is performed at a temperature of 10° to 60° and at a pH of 4 to 10.

* * * * *